US006448559B1

(12) United States Patent
Saoudi et al.

(10) Patent No.: US 6,448,559 B1
(45) Date of Patent: Sep. 10, 2002

(54) DETECTOR ASSEMBLY FOR MULTI-MODALITY SCANNERS

(75) Inventors: Abdelhamid Saoudi, Ottawa; Roger Lecomte, Sherbrooke, both of (CA)

(73) Assignee: Université de Sherbrooke, Sherbrooke (CA)

( * ) Notice: Subject to any disclaimer, the term of this patent is extended or adjusted under 35 U.S.C. 154(b) by 0 days.

(21) Appl. No.: 09/434,480

(22) Filed: Nov. 5, 1999

(30) Foreign Application Priority Data

Nov. 6, 1998 (CA) .............................................. 2252993

(51) Int. Cl.$^7$ ................................................ G01T 1/20
(52) U.S. Cl. .............. 250/367; 250/370.09; 250/370.11
(58) Field of Search ................................. 250/367, 370, 250/370.09, 370.11

(56) References Cited

U.S. PATENT DOCUMENTS

| | | | |
|---|---|---|---|
| 4,843,245 A | | 6/1989 | Lecomte ...................... 250/367 |
| 4,958,080 A | * | 9/1990 | Melcher ................... 250/483.1 |
| 5,103,098 A | | 4/1992 | Fenyves ...................... 250/368 |
| 5,155,365 A | | 10/1992 | Cann et al. ................... 250/363 |
| 5,210,421 A | * | 5/1993 | Gulberg ................. 250/363.04 |
| 5,338,936 A | | 8/1994 | Gullberg et al. ............. 250/363 |
| 5,376,795 A | | 12/1994 | Hasegawa et al. ........... 250/363 |
| 5,391,877 A | | 2/1995 | Marks ......................... 250/363 |
| 5,399,869 A | * | 3/1995 | Usuda ...................... 250/486.1 |
| 5,532,122 A | * | 7/1996 | Drukier ....................... 250/367 |
| 5,585,637 A | | 12/1996 | Bertelsen et al. ............ 250/363 |
| 5,608,221 A | | 3/1997 | Bertelsen et al. ............ 250/363 |
| 5,672,877 A | | 9/1997 | Liebig et al. ................ 250/363 |

OTHER PUBLICATIONS

The Design and Performance eof a Simultaneous Transmission and Emission Tomography System; Gullberg et al., IEEE Transactions onNuclear Science, vol. 45, No. 3, Jun. 1998.

Simultaneous Spect and CT with an Opposed Dual Head Gamma Camera System and Conventional Parallel Hole Collimators; Kimiaei et al., IEEE Transactions on Nuclear Science, vol. 43, No. 4, Aug. 1996.

Development of a Pet Detector System Compatible with MRI/NMR Systems; Shao et al., IEEE Transacitons on Nuclear Science, vol. 44, No. 3, Jun. 1997.

Simultaneous Pet and MR Imaging; Shao et al.; Phys. Med. Biol. 42 (1997) 1965–1970 Printed in the UK.

Combined MRI–Pet Scanner: A Monte Carlo Evaluation of the Improvements in Pet Resolution Due to the Effects of a Static Homogeneous Magnetic Field; Raylman et al., IEEE Transactions on Nuclear Science, vol. 43, No. 4, Aug. 1996.

Clinical Applications of Registration and Fusion of Multimodality Brain Images from Pet, Spect, CT, and MRI; Pietrzyk et al., European Journal of Radiology 21 (1996) 174–182.

Performance of a YSO/LSO Phoswich Detector for use in a Pet/Spect System; Dahlbom et al., IEEE Transactions on Nuclear Science, vol. 44, No. 3, Jun. 1997.

\* cited by examiner

*Primary Examiner*—Georgia Epps
*Assistant Examiner*—M. Hasan
(74) *Attorney, Agent, or Firm*—Goudreau Gage Dubuc

(57) ABSTRACT

A detector assembly for multi-modality PET/SPEC/CT scanners comprises a first layer for detecting low energy gamma radiation and X-rays and a second layer for detecting high energy gamma radiation. The first layer is generally transparent to high energy gamma radiation. The second layer may advantageously provide measurement of depth of interaction of the high energy radiation. The first layer is preferably in the form of a thin CsI(Tl) scintillator, while the second layer includes a pair of LSO/GSO scintillators. The detector assembly includes a photodetector, preferably in the form avalanche photodiode to transform the light signals from the scintillators into electric signals. The detector assembly is advantageously incorporated in a multi-modality PET/SPECT/CT scanner allowing simultaneous transmission and emission imaging with the same detection geometry.

26 Claims, 4 Drawing Sheets

DETECTOR ASSEMBLY FOR MULTI-MODALITY SCANNERS

FIELD OF THE INVENTION

The present invention relates to multi-modality scanners. More specifically, the present invention is concerned with a detector assembly for multi-modality scanners, in particular but not exclusively, an APD (Avalanche PhotoDiode)—based detector for multi-modality PET(Positron Emission Tomography)/SPECT(Single Photon Emission Computed Tomography)/CT(Computerized Tomography) scanners.

BACKGROUND OF THE INVENTION

The lack of anatomical information and the lack of information about the photon attenuation in the body in emission tomography imaging like SPECT (Single Photon Emission Computed Tomography) or PET (Positron Emission Tomography) imaging are major factors limiting the ability to accurately quantify radionuclide uptake in small Regions Of Interest (ROI). Such lack of information about anatomical retails and photon attenuation limits the diagnostic utility of emission imaging.

A drawback of emission tomography is that the spatial resolution obtained is limited. Typical emission tomographs have a resolution of the order of 5 to 15 mm. Another important drawback is that the images produced are very noisy since the doses of radioisotopes that can be injected and the maximum counting rate are both limited. These two drawbacks render the delimitation of the regions of interest difficult.

Transmission imaging presents the advantage to have a sub-millimetric spatial resolution and thus allows to uncover anatomical details of the organ of interest. A drawback of transmission imaging is that it provides very little functional information.

The trivial solution to overcome the above mentioned drawbacks of each imaging method is to gather CT (transmission) and SPECT or PET (emission) images and to merge the anatomical and functional information. A way to achieve this is to collect the two sets of data using two different apparatuses, one gathering anatomical information and the other functional information, and to co-register one set with the other using sophisticated software.

A drawback of the latter method is that the patient must be moved from one scanner to the other between the two scans. Moreover, the two scans will most often be obtained several days apart, subject to scanner availability. As a consequence, it is usually difficult to superimpose the two sets of data since the measurements are made separately, at different times, using scanners having two different geometries and two different resolutions. Movements of the patient as well as changes of the anatomy over time can cause significant mismatch between the resulting images.

A combined PET/CT tomograph has been developed jointly by the PET Facility at the Pittsburgh Medical center and CTI PET Systems Inc. This tomograph was described at the following World Wide Web address: T. Beyer, D. W. Townsend, T. Brun, P. E. Kinahan, M. Charron, R. Roddy J. Jerin, J. Young, L. Byars, R. Nutt, "A combined PET/CT scanner for clinical oncology", Journal of Nuclear Medicine 41(8):1369–79, 2000 Aug. , on Mar. 31$^{st}$, 1998. The structure of the proposed tomograph allows acquiring sequentially anatomical (CT) and functional (PET) information and does not require the patient to be moved between scans.

A drawback of the latter tomograph is that it can be difficult to superimpose the two sets of data since the measurements are done separately, with two different resolutions and two different geometries. Moreover, movements of the patient as well as movements of the non-rigid structures within the body such as in the thorax or the abdomen add a blur to the resulting images.

The article entitled "The Design and Performance of a Simultaneous Transmission and Emission Tomography System", published in IEEE Transactions on Nuclear Science, Vol. 45, No 3, June 1998, and authored by Guliberg et al. proposes a simultaneous transmission and emission tomography system. The system includes a detector to collect data from transmission and emission sources at different energies, and two other detectors To simultaneously acquire emission data.

A drawback of the system of Gullberg et al. is that the incorporation of a transmission-computed tomography system into a three-detector SPECT system causes problems of transmission data truncation and crosstalk between transmission and emission data windows. Another drawback relates to the used detectors which are limited in count rate and which cannot collect sufficient number of events in a short time for accurate anatomical definition of the body structures. Furthermore, movements of the patient can still cause blur.

In U.S. Pat. No. 5,376,795, issued on Dec. 27, 1994, Hasegawa et al. describe an emission-transmission imaging system that uses a single detector for the transmission and emission data. The detector operates in a count or pulse mode to allow discrimination between the emission and transmission photons at low or medium count rates. At high count rate (with an X-ray tube, for instance) the detector can operate in a current mode without energy resolution. One advantage of this system is that both the transmission and the emission images are obtained by the same detector and. thus, are intrinsically aligned. One drawback of the system of Hasegawa et al. is that it cannot be used to produce PET emission imaging.

OBJECTS OF THE INVENTION

An object of the present invention is therefore to provide a multi-modality scanner that possesses none of the above mentioned drawbacks of the prior art.

Another object of the invention is to provide a detector assembly for multi-modality PET/SPECT/CT scanners.

SUMMARY OF THE INVENTION

More specifically, in accordance with the present invention, there is provided a detector assembly for multi-modality scanners for detecting low and/or high energy radiation emitted from a source under investigation. This detector assembly comprises a low energy radiation detector substantially transparent to high energy radiation but responsive to low energy radiation from the source. This low energy radiation detector therefore produces, in response to the low energy radiation, first radiation characterizing signals. The detector assembly also comprises a high energy radiation detector located downstream the low energy radiation detector and responsive to high energy radiation from the source. This high energy radiation detector produces, in response to the high energy radiation, second radiation characterizing signals.

Since the detector assembly comprises a low energy radiation detector substantially transparent to high energy radiation and a high energy radiation detector located downstream the low energy radiation detector, this detector assembly is suitable for conducting PET, SPECT and CT tomography either independently or simultaneously.

According to a preferred embodiment of the invention, at least one of the low and high energy radiation detectors comprises a scintillator, and the detector assembly further comprises a photodetector optically coupled to the scintillator. This photodetector produces, in response to the radiation characterizing signals from the scintillator, corresponding electric signals. The photodetector is advantageously selected form the group consisting of an avalanche photodiode, a pin diode and a photomultiplier tube.

In accordance with other preferred embodiments of the subject invention:

- the low energy radiation detector comprises a high-luminosity scintillator, this high-luminosity scintillator preferably being a CsI(Tl) scintillator;
- the high energy radiation detector includes at least one high-density scintillator, this high-density scintillator preferably comprising a LSO scintillator and a GSO scintillator;
- the LSO scintillator is located downstream of and is optically coupled to the CsI(Tl) scintillator, and the GSO scintillator is located downstream of and is optically coupled to the LSO scintillator;
- the low energy radiation includes X-rays, the high energy radiation includes high energy gammas, the low energy radiation further includes low energy gammas, and the high energy radiation further include& low energy gammas.

The present invention further relates to a multi-layer detector assembly for multi-modality scanners for detecting X-rays and/or high energy gammas emitted from a source under investigation. The detector assembly comprises a first X-ray detecting layer substantially transparent to high energy gammas and producing, in response to X-rays from the source, X-ray characterizing signals, and a second high energy gamma detecting layer located downstream the first layer and producing, in response to high energy gammas from the source, gamma characterizing signals.

Preferably, at least one of the first and second layers is a scintillator and the characterizing signals produced by the scintillator include scintillation, and the multi-layer detector assembly further comprises a photodetector layer which produces, in response to the scintillation, a corresponding electric signal.

According to another aspect of the present invention, there is provided a multi-modality scanner comprising a gantry having a longitudinal axis. a scanner operation controller, and at least one pair of diametrically opposite detector assemblies as described hereinabove. The two diametrically opposite detector assemblies mutually face each other and are connected to the scanner operation controller whereby the first and second radiation characterizing signals from the detector assemblies are supplied to the scanner operation controller. The multi-modality scanner further comprises a low energy gamma radiation source movably mounted to the gantry and a collimator mounted rotatable to the gantry about the longitudinal axis. Both the low energy gamma radiation source and the collimator are connected to and controlled by the scanner operation controller.

The objects, advantages and other features of the present invention will become more apparent upon reading of the following non restrictive description of a preferred embodiment thereof, given by way of example only with reference to the accompanying drawings.

DESCRIPTION OF THE PREFERRED EMBODIMENT

Generally stated, a detector assembly according to the present invention comprises a plurality of detectors that share a common geometry by being positioned on top of each other, therefore forming a layered detector assembly. Each layer is configured and sized so as to detect a specific radiation spectra and to be generally transparent to radiations intended to be detected by layers located downstream therefrom, i.e. further from the radiation source.

Figure 1:
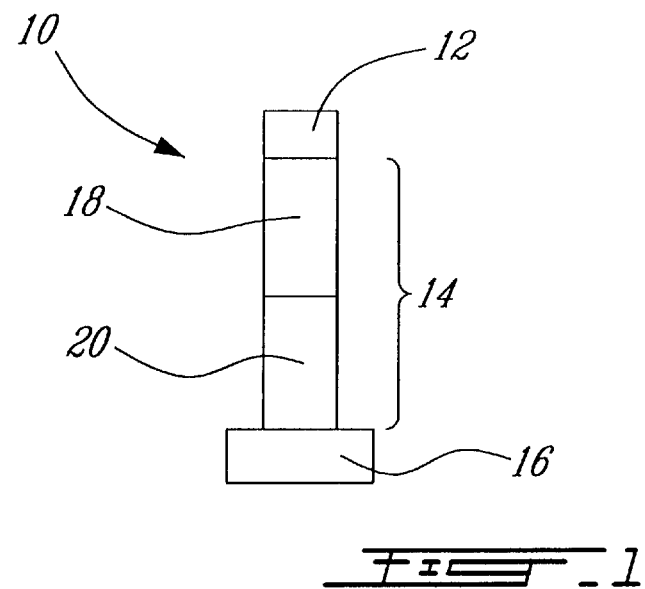
FIG. 1 is a schematic view of a detector assembly for multi-modality scanners according to a preferred embodiment of the present invention.

A detector assembly 10 according to a preferred embodiment of the present invention will now be described in connection with FIG. 1 of the appended drawings.

The detector assembly 10 comprises a first layer 12 for detecting low energy radiation such as, for example, X-rays (or low energy gammas) and medium energy gammas, a second layer 14 for detecting high energy radiation, such as, for example, high energy gammas and a receiver 16 for collecting the signals from the first and second layers 12 and 14.

It is to be noted that expressions such as "low energy radiation" and "high energy radiation" are not used herein to limit the scope of the present invention. These expressions are intended to express the relative energy of different radiations.

Conventionally X-rays are used in CT imaging, medium energy gammas (typically having an energy of 140 keV) are used in SPECT imaging and high energy gammas (typically having an energy of 511 keV) are used in PET imaging.

When the detector assembly 10 is used in a multi-modality PET/SPECT/CT scanner, the first layer 12 is advantageously in the form of a thin high-luminosity scintillator such as, for example, a thin CsI(Tl) (Cesium Iodide (thallium at a concentration of $10^{-3}$ on a per mole basis)) scintillator, while the second layer 14 is in the form of a pair of high-density scintillators 14. The second layer 14 is so configured and sized as to provide depth-of-interaction information for the PET modality.

The thickness of high-luminosity scintillator 12 is chosen so as to absorb as completely as possible the X-rays used in CT and to absorb as little as possible of the high energy 511 keV gammas from PET radio tracers.

The pair of high density scintillators 14 advantageously includes a LSO scintillator 18 and a GSO scintillator 20. The LSO scintillator 18 is used to absorb as completely as possible the low-energy gammas which are not completely absorbed in the CsI(Tl) scintillator 12. The LSO/GSO pair 14 is so chosen as to discriminate scintillation decay times from high energy gammas. Alternatively, a pair of LSOs, with short and long decay times, or any other combination and number of scintillators with suitable chosen decay times, could be used instead of the LSD/GSO pair 14.

The LSO scintillator 18 is mounted on top of the GSO scintillator 20, and the CsI(Tl) scintillator 12 is mounted on top of the LSO scintillator 18. The three scintillators 12, 18 and 20 are secured to one another and to the photodetector 16 by conventional means well known to those of ordinary skills in the art and are optically coupled using optical coupling compound, such as, for example, optical grease.

The detector assembly 10 is configured to be used with the CsI(Tl) scintillator 12 facing the patient or other object on which measurement is made. The CsI(Tl) scintillator 12 is sufficiently thin to be substantially transparent to high energy photons (typically 511 keV), but sufficiently thick to completely absorb low-energy X-rays and at least partially absorb medium energy gammas. The CsI(Tl) scintillator 12 is therefore substantially transparent to the high energy annihilation gammas of PET.

Each layer 12, 18 or 20 generates signals collected by the receiver 16 for being. subsequently discriminated. Since signals generated by scintillators are in the form of scintillation, the receiver 16. advantageously comprises a photodetector that both collects scintillation from the different layers and transforms scintillation light in electric signals. Examples of photodetectors include avalanche photodiodes (APD), photomultiplier tubes, pin diodes, etc.

A first layer 12 made of a CsI(Tl) scintillator presents the advantage of having a scintillation decay time sufficiently different to enable the photodetector 16 to discriminate its signature from those of the LSO and GSO scintillators 18 and 20. As will be seen hereinbelow, the photodetector 16 uses pulse shape discrimination (PSD) methods for that purpose.

CsI(Tl), LSO and GSO scintillators as well as photodetectors are believed to be well known to those of ordinary skill in the art and, accordingly, will not be further described herein.

Of course, any other combination of suitable scintillatore with the desired gamma absorption and decay time characteristics can be used.

Another alternative is to choose a first layer 12 substantially transparent to high and medium energy gammas but suitable for detecting X-rays, and to choose a second layer suitable for detecting medium and high energy gammas.

Although the above described preferred embodiment of the detector assembly 10 comprises scintillators, other detectors such as for example semiconductor detectors, including CdTe and CdZnTe based detectors, can be used without departing from the spirit and nature of the present invention.

Figure 2:
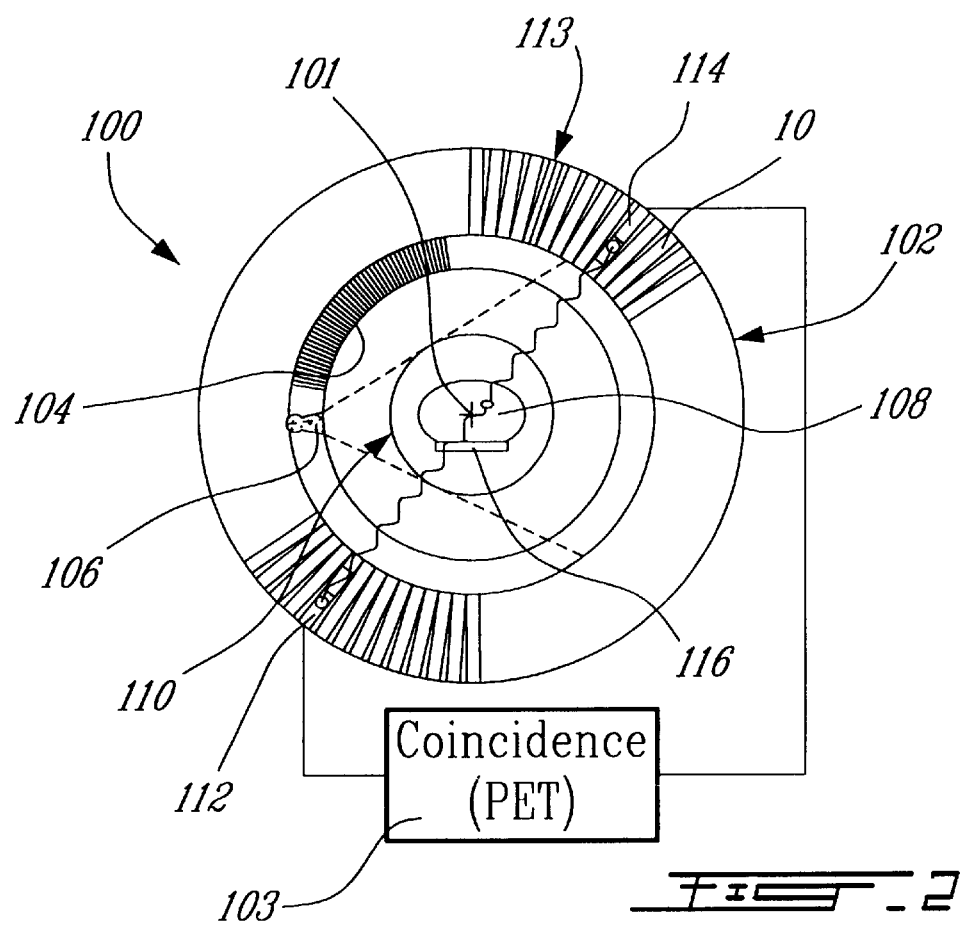
FIG. 2 is a schematic view of a multi-modality scanner using the detector assembly of FIG. 1.

Turning now to FIG. 2, a multi-modality PET/SPECT/CT scanner 100, using detector assemblies such as detector assembly 10, will be described.

The scanner 100 comprises a cylindrical gantry 102 having a longitudinal axis 101, provided with two diametrically opposite sets of detector assemblies 10, a collimator 104, an external source 106 to produce low energy radiation and a controller (not shown).

FIG. 2 illustrates a patient 108 who is investigated by means of the scanner 100. The patient 108 therefore constitutes, in the presently described preferred embodiment of the invention, the source under investigation which emits low and/or high energy radiation. The scanner 100 is obviously provided with a frame or other means (not shown) on which the gantry 102 is mounted.

Each of the detector assemblies 10 are fixedly mounted to the gantry 102 with the CsI(Tl) scintillator 12 turned inwardly to face the field of view 110, to form a detector ring 113. Each detector assembly such as 112 of one set is positioned diametrically opposite to a detector assembly such as 114 of the second set relative to the field of view 110. The opposite pairs of detector assemblies such as 112 and 114 enable coincidence for PET imaging. Each detector assembly 10 is connected to the controller (not shown).

A collimator 104 is required for SPECT imaging. It is placed in front of the detector assemblies 10, between these detector assemblies 10 and the patient 108, to define preferential directions of incidence of the medium-energy photons (typically 140 keV) used for SPECT imaging. The collimator 104 can be a section of arc, as shown in FIG. 2. The collimator 104 is then rotated about axis 101 inside the detector ring 113 to obtain projections over different incidence angles sequentially, using only a fraction of the detector assemblies over the ring. In such case, the detector assemblies of the ring 113 which are not used for SPECT imaging can be used for PET and/or CT imaging simultaneously. The collimator 104 is connected to the controller (not shown) through conventional link means such as electric cables. This enables the controller to command the collimator 104.

Alternatively, the collimator 104 can form a fixed full ring that fits inside the detector ring 113 to perform SPECT imaging using all the detector assemblies 10 at the same time. In either case, the collimator 104 must be retractable axially from inside the ring 113 of detector assemblies to permit PET or CT imaging with the full ring 113 of detector assemblies when SPECT imaging is not used.

The external source 106 is used for CT imaging. It can be in the form of an X-ray tube or of a high intensity radionuclide source emitting low-energy photons (X-rays or low energy gammas). As illustrated in FIG. 2, the source 106 is mounted in the spacer between the inner face of the detector ring 113 and the field of view 110. Alternatively the source 106 can be embedded or incorporated into the structure of the gantry 102. In the latter case, the gantry 102 must be further provided with an inner aperture to enable projection of the X-rays in the direction of the patient 108. In either case, a mechanism (not shown) is provided to rotate the source 105 around the patient in order to obtain projection data over all incidence angles for CT image acquisition. The X-ray tube 106 is controlled through the controller (not shown). For that purpose. the X-ray tube 106 is connected to the controller through electric cables (not shown) or other link means. X-ray tubes are believed to be well known to those of ordinary skill in the art and will not be further described herein.

Alternatively, the external source 106 can be a radioactive element having a high activity. An example is a high intensity, low energy radionuclide source with the associated shielding, collimation and shutter mechanisms currently used for CT imaging.

The controller (not shown) can be a computer, or another electronic device provided with circuitries and/or programs to gather, amplify, discriminate and characterize the signals produced by the detector assemblies 10. A display can be connected to the controller (not shown) to show the resulting images. Construction of the controller and display is believed to be within the ability of one of ordinary skill in the art and, accordingly, will not be further discussed.

In operation, a patient 108 is first positioned on a table 116 situated approximately in the center of the gantry 102. Restraining means such as straps (not shown) can be used to immobilize the patient 108 on the table 116. The. patient 108 has been previously injected with a small amount of radiotracer that targets the tissue or the organ of interest. The radiotracer can contain two types of radioisotope: one for PET imaging and the other for SPECT imaging.

A PET radiotracer produces high energy gamma photons which are emitted in pairs collinearly in opposite directions. The energy of each photon is approximately 511 keV. They are detected in coincidence by two diametrically opposite detector assemblies 10 (see for example detector assemblies 112 and 114). These photons pass through the CsI(Tl) scintillators 12 that are substantially transparent to these high energy photons. The photons are then detected by the LSO/GSO pairs 14. A signal is then sent to the controller that accordingly includes a coincidence circuit (see 103 in FIG. 2). This signal is characterized by a pulse amplitude, a scintillation decay time and a depth-of-interaction. This information is used to discriminate the type of interaction and its origin. The depth-of-interaction is also used to increase the spatial resolution of the image that will be produced by the controller.

The radiotracer can also produce mono-photonic gammas for the SPECT imaging. The energy of these photons is lower than the energy of the PET photons and generally higher or similar to the energy of the CT photons. The direction of propagation of the photons is determined by the collimator 104. The collimator 104 is configured taking into consideration the energy of the radiotracer and the type of measurement.

A SPECT photon can be detected by both the CsI(Tl) scintillator 12 and by the LSO 18 of the LSO/GSO pair 14. The signals produced by the detector assembly 10 are characterized by a pulse amplitude and a scintillation decay time.

The CsI(Tl) scintillator 12 also detects photons coming from the external source 106 after crossing the region of interest without being absorbed or scattered through a large angle. This type of interaction is believed to be well Known to those of ordinary skill in the art and, accordingly, will not be described in further detail.

For CT imaging, the detector assemblies 10 are either operated in integration mode or in counting mode. To limit the irradiation of the patient 108 and the background noise, the external source 106 can also be collimated in the direction of detector assemblies 10. Likewise, to limit the background noise, especially the one due to scatter radiation from within the patient 108, a fan beam or cone beam collimator with focal point at the source position can be used in front of the detectors. In another embodiment of the present invention, the same collimator used for SPECT imaging having the appropriate focal length can also be used for CT.

It should be noted that the scintillation signals from the three types of scintillators of the detector assembly 10 are converted to electric currents by the photodetector 16 and then into voltage pulses by the controller.

A conventional technique, such as for example pulse shape discrimination (PSD), can be used to discriminate detected events according to energy and/or pulse shape as will be explained in more detail hereinbelow.

Alternatively, discrimination of the detected events can be accomplished by shape discrimination of the scintillation rise time of each scintillator 12, 18 or 20, by a combination of shape and amplitude discrimination of the scintillation pulse on each scintillator, or by individual readouts of each scintillator 12, 18 or 20.

Those of ordinary skill in the art will appreciate that CsI(Tl) signals can be easily discriminated from the LSO/GSO signals by classical pulse shape discrimination techniques.

It should be noted that each detector assembly 10 advantageously represents a picture element (pixel) providing the multi-modality PET/SPECT/CT scanner 100 with a high counting rate. The detector assemblies 10 which represent pixels can then be arranged into 1-D or 2-D close-packed arrays with individual readout and circuitry for independent processing of the signals from each detector pixel. One significant advantage of the detector assembly 10 when used in combination within large detector arrays is the very high overall count rate capability of the system, since the signals from every individual detector assembly 10 are processed in parallel by independent circuits.

Merging of the anatomical and functional images is automatic since both modalities share the same detector geometry and are intrinsically aligned. The CT information can thus be used independently or for attenuation correction of the emission imaging (PET/SPECT).

One of the advantages of the detector assembly 10 according to this invention is its discrimination properties that allow a same detector assembly 10 to gather simultaneously PET, SPECT and CT images.

Experiments have been conducted to show these discrimination properties. The tested detector assemblies were similar to the detector assembly 10 of FIG. 1.

A 5×5 mm$^2$ active area reverse avalanche photodiode (APD) operated at an internal gain of 125 was used as detector 16 throughout this experiment. All crystals of the scintillators were polished on all faces and had a 4×4 mm$^2$ cross section. A 3 mm thick CsI(Tl) crystal 12 was placed on top of an LSO crystal 18 itself placed on top of a GSO crystal 20, both LSO and GSO crystals having a length of 10 mm. All these crystals were coupled together with optical grease and wrapped in several layers of Teflon tape. The assembly was mounted on the APD through the GSO end also using optical grease. Signals from the APD were collected by a charge sensitive preamplifier, shaped with a spectroscopic amplifier having a shaping time of 250 ns and processed with a zero cross time PSD circuit. Measurements were performed using radioactive sources of $^{88}$Ge (511 keV), $^{99m}$Tc (140 keV) and $^{41}$Am (60 keV). Similar results can be obtained by using other PSD methods such as the dual charge integration, the delayed charge integration or the dual amplitude sampling techniques, which are all well known in the art.

The discrimination features of the APD-GSO/LSO/CsI (Tl) detector assembly 10 are illustrated in FIGS. 3 to 8 and summarized in Table 1. In this Table, ΔE (%) is the energy resolution or width at half of maximum height, in percent relative to the peak position, of the full energy photopeak in the pulse height spectra of each individual scintillator; $\Delta t_{PSD}$ is the time resolution or width at half of maximum height, in nanoseconds, of the zero cross time peak of each individual scintillator in the zero cross time spectra; and Zero Cross Time is the position, in nanoseconds, of the time peak of each individual scintillator in the zero cross time spectra.

TABLE 1

Results of pulse height discrimination (PHD) and pulse shape discrimination (PSD) measurements.

|  |  | GSO/LSO/CsI(Tl) | | |
| --- | --- | --- | --- | --- |
|  |  | GSO | LSO | CsI(Tl) |
| 511 keV | $\Delta E$ (%) | 14 | 13 | 9.5 |
|  | $\Delta t_{PSD}$ (ns) | 10 | 4 | 18 |
|  | Zero Cross (ns) | 38 | 24 | 130 |
| 140 keV | $\Delta E$ (%) | 22 | 21 | 14 |
|  | $\Delta t_{PSD}$ (ns) | — | ~15 | 38 |
|  | Zero Cross (ns) | 38 | 24 | 130 |
| 60 keV | $\Delta E$ (%) | — | 31 | 21 |
|  | $\Delta t_{PSD}$ (ns) | — | ~20 | 64 |
|  | Zero Cross (ns) | — | ~20* | 102 |

*PSD time peaks overlap.

Table 1 and FIGS. 3 to 8 show that the CsI(Tl) scintillator can be easily discriminated and yields suitable energy resolution in an APD-based detector assembly designed for PET/SPECT/CT multi-modality imaging.

Table 1 and FIGS. 3 to 6 show that the LSO scintillator can be easily discriminated from GSO and CsI(Tl) at 511 keV and from CsI(Tl) at 140 keV. The fact that LSO is not fully discriminated from GSO at 140 keV is not harmful since 140 keV photons are very unlikely to reach the GSO scintillator located at the back of the detector assembly after crossing the front layers of CsI(Tl) and LSO. Similarly, the fact that LSO can be merely discriminated from CsI(Tl) at 60 keV has no consequence since X-rays are not expected to reach LSO behind the front layer of CsI(Tl). The LSO scintillator is shown to yield suitable energy resolution at 511 keV and acceptable energy resolution at 140 keV in an APD-based detector assembly designed for PET/SPECT/CT multi-modality imaging.

Figure 3:
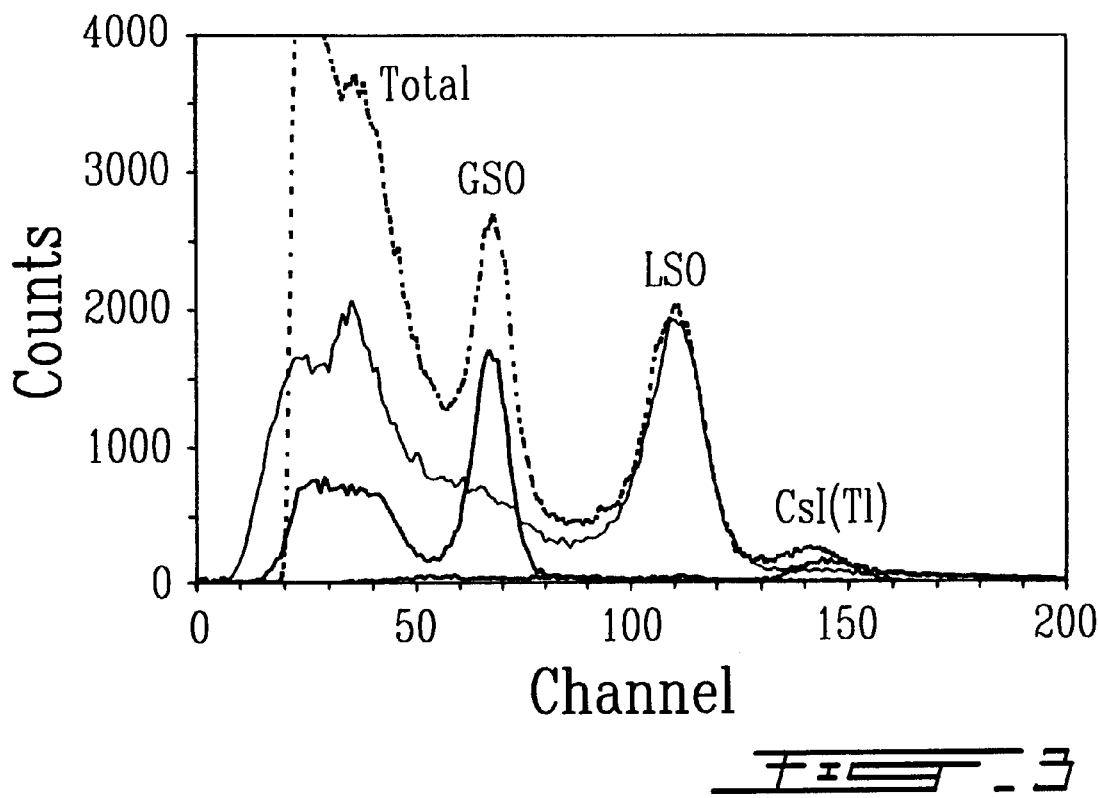
FIG. 3 is a graph showing the total and PSD (Pulse Shape Discrimination)-gated energy spectra, by the zero cross time technique, of high energy (511 keV) annihilation radiation sensed with the detector assembly of FIG. 1.
Figure 4:
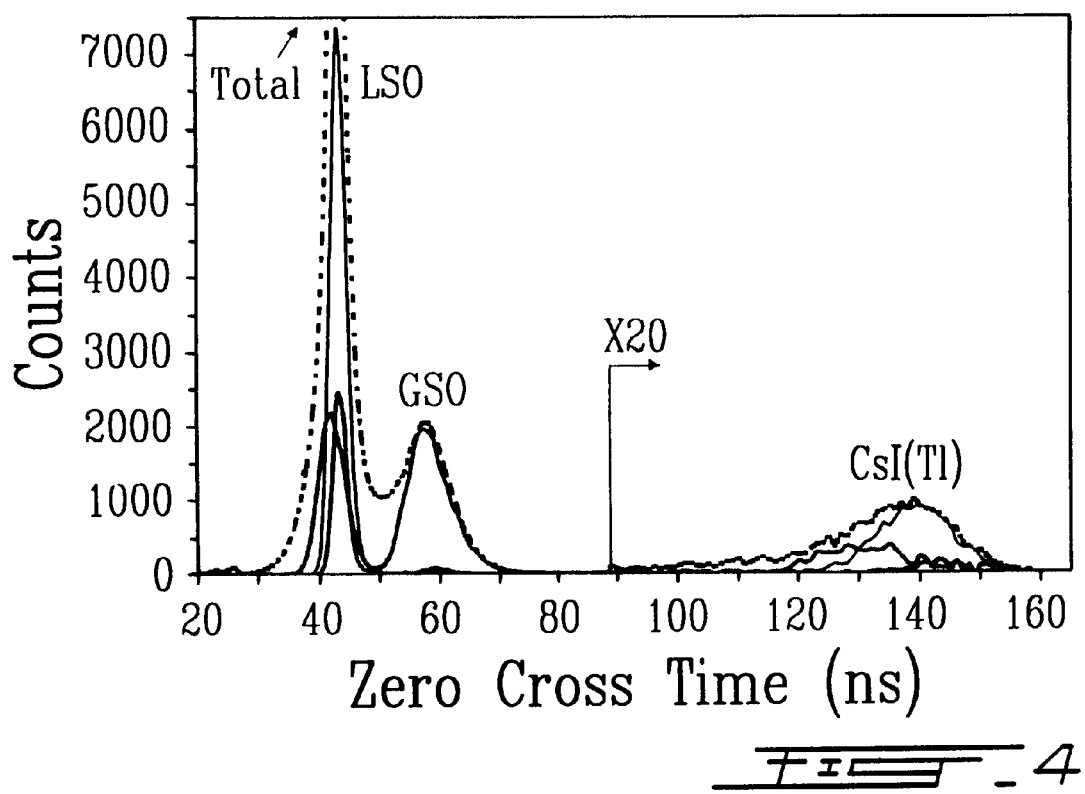
FIG. 4 is a graph showing the total and energy-gated zero cross time spectra of high energy (511 keV) annihilation radiation sensed with the detector assembly of FIG. 1.
Figure 5:
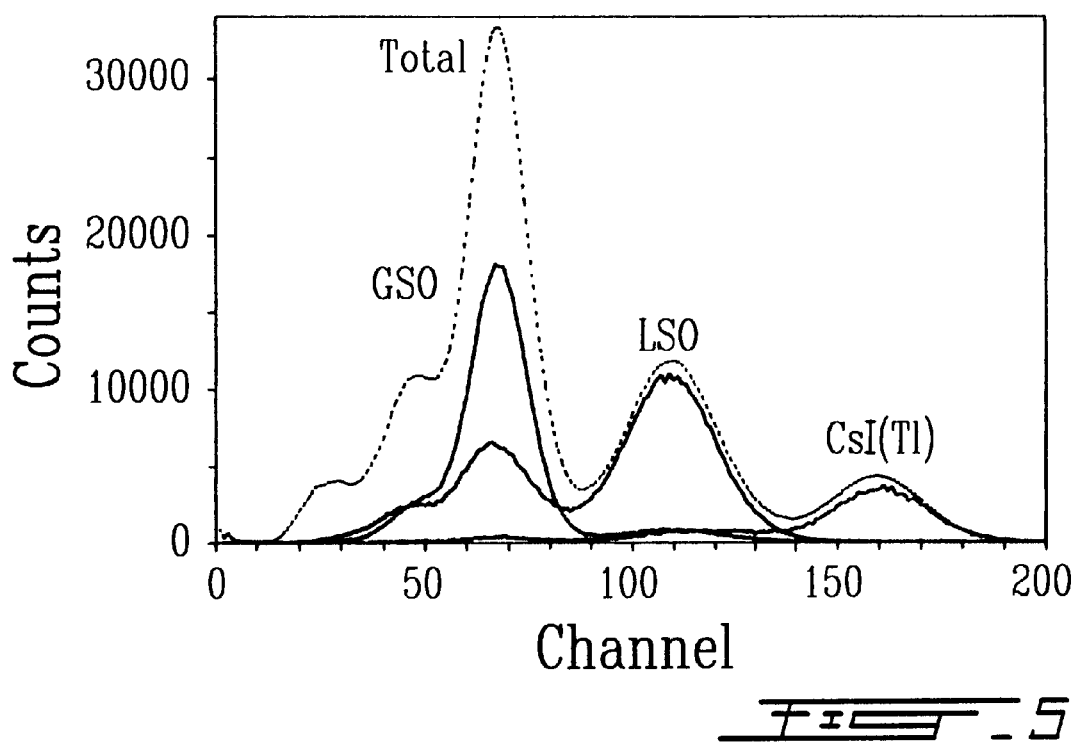
FIG. 5 is a graph showing the total and PSD-gated energy spectra of medium energy gammas (140 keV) sensed with the detector assembly of FIG. 1;.
Figure 6:
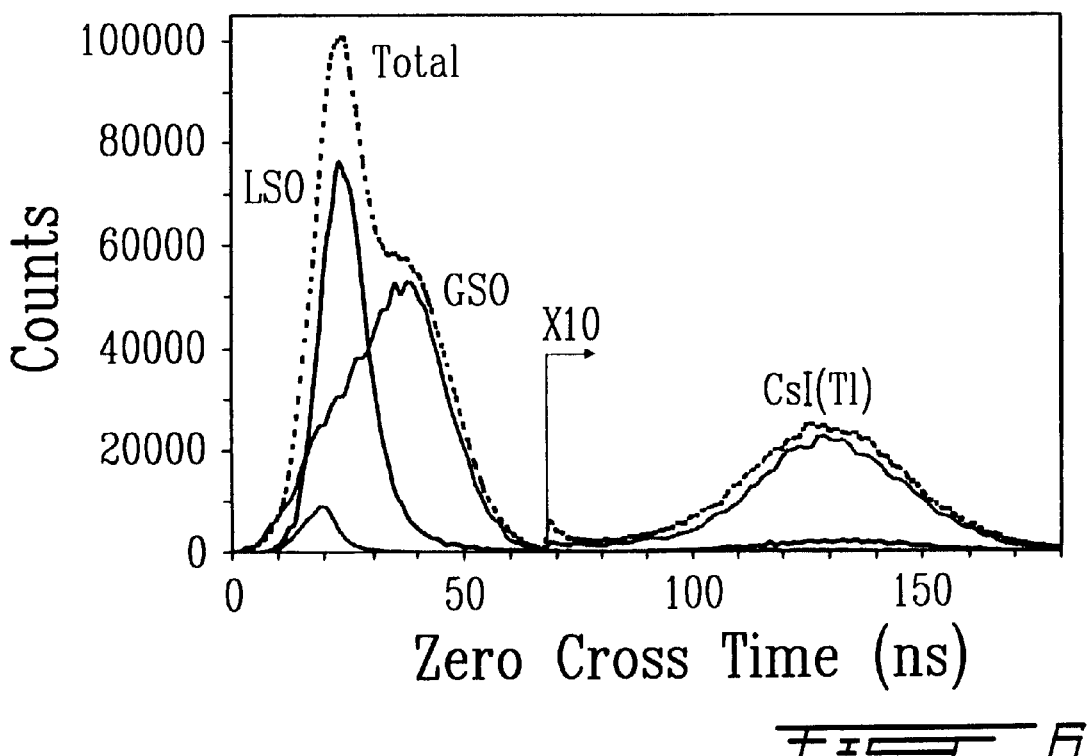
FIG. 6 is a graph showing the total and energy-gated zero cross time spectra of medium energy gammas (140 keV) sensed with the detector assembly of FIG. 1.
Figure 7:
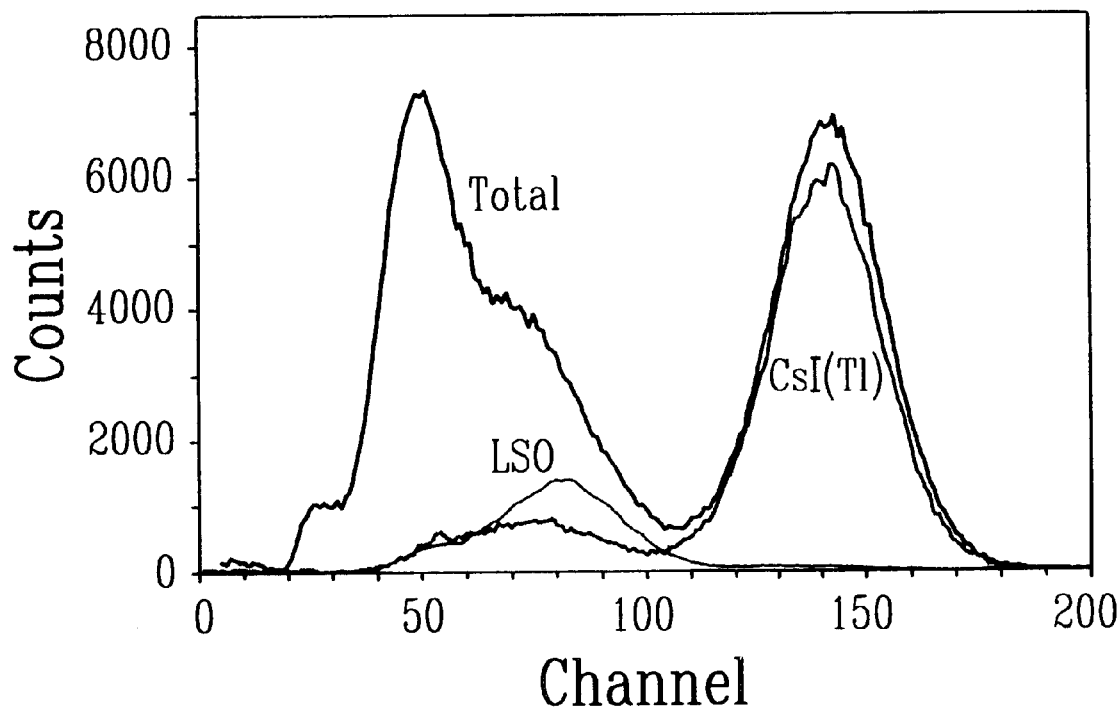
FIG. 7 is a graph showing the total and PSD-gated energy spectra of X-rays (60 keV) sensed with the detector assembly of FIG. 1.
Figure 8:
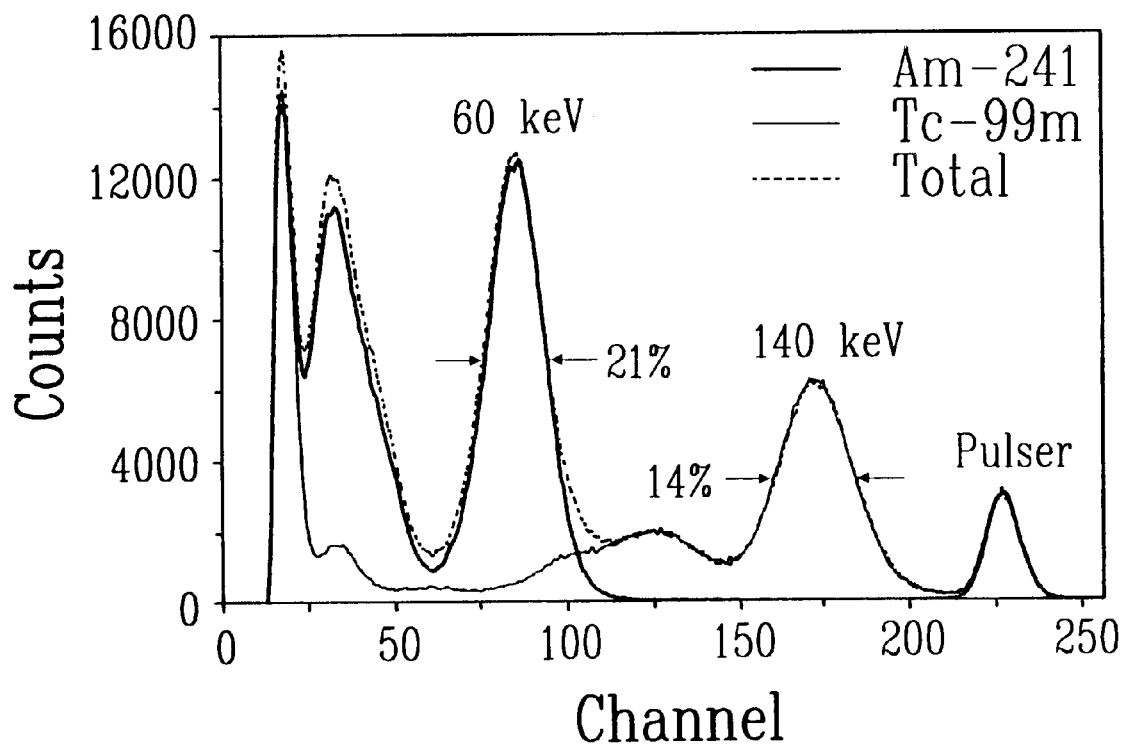
FIG. 8 is a graph showing the energy spectra of X-rays (60 keV) and medium energy gammas (140 keV) sensed with the detector assembly of FIG. 1 and illustrating the separation that can be obtained between X-rays and medium energy gammas in the CsI(Tl) layer.

Finally, Table 1 and FIGS. 3 and 4 show that the GSO scintillator can be easily discriminated from LSO and CsI (Tl) at 511 keV and that it yields suitable energy resolution at 511 keV in an APD-based detector assembly designed for PET/SPECT/CT multi-modality imaging.

Although the present invention has been described hereinabove by way of preferred embodiments thereof, it can be modified at will, within the scope of the appended claims, without departing from the spirit and nature of the subject invention.

What is claimed is:

1. A detector assembly for multi-modality scanners for detecting low energy radiation and low and high energy gammas emitted from a source under investigation, the detector assembly comprising;
    a low energy radiation detector substantially transparent to the low and high energy gammas but responsive to the low energy radiation from the source, said low energy radiation detector producing, in response to said low energy radiation, first radiation characterizing signals;
    a low energy gamma detector located downstream from said low energy radiation detector and responsive to low energy gammas from the source, said low energy gamma detector producing, in response to said low energy gammas, second radiation characterizing signals; and
    a high energy gamma detector located downstream from said low energy gamma detector and responsive to high energy gammas from the source, said high energy gamma detector producing, in response to the high energy gammas, third radiation characterizing signals.

2. A detector assembly as recited in claim 1, wherein at least one of said low energy radiation detector, said low energy gamma detector and said high energy gamma detector comprise a scintillator.

3. A detector assembly as recited in claim 2, further comprising a photodetector optically coupled to said scintillator, said photodetector producing, in response to the radiation characterizing signals from said scintillator, corresponding electric signals.

4. A detector assembly as recited in claim 3, wherein the photodetector is selected form the group consisting of an avalanche photodiode, a pin diode and a photomultiplier tube.

5. A detector assembly as recited in claim 3, wherein the low energy radiation detector comprises a high-luminosity scintillator.

6. A detector assembly as recited in claim 5, wherein said high-luminosity scintillator is a CsI(Tl) scintillator.

7. A detector assembly as recited in claim 1, wherein said low energy gamma detector includes a first high-density scintillator.

8. A detector assembly as recited in claim 7, wherein said first high-density scintillator comprises a LSO scintillator.

9. A detector assembly for multi-modality scanners for detecting low and/or high energy radiation emitted from a source under investigation, the detector assembly comprising:
    a low energy radiation detector substantially transparent to the high energy radiation but responsive to low energy radiation from the source, said low energy radiation detector producing, in response to the low energy radiation, first radiation characterizing signals, said low energy radiation detector comprising a CsI(Tl) scintillator;
    a high energy radiation detector located downstream from the low energy radiation detector and responsive to the high energy radiation from the source;
    said high energy radiation detector producing, in response to the high energy radiation, second radiation characterizing signals;
    said high energy radiation detector including a LSO scintillator downstream of and optically coupled to the CsI(Tl) scintillator and a GSO scintillator downstream of and optically coupled to the LSO scintillator; and
    a photodetector optically coupled to at least one of said scintillators said photodetector producing, in response to the radiation characterizing signals from said at least one of said scintillators, corresponding electric signals.

10. A detector assembly as recited in claim 1, wherein the low energy radiation includes X-rays.

11. A detector assembly as recited in claim 10, wherein said low energy radiation further includes low energy gammas.

12. A multi-layer detector assembly for multi-modality scanners for detecting X-rays and low and high energy gammas emitted from a source under investigation, said detector assembly comprising:

an X-ray detecting layer substantially transparent to low and high energy gammas and producing, in response to X-rays from the source, X-ray characterizing signals;

a low energy gamma detecting layer located downstream from said X-ray detecting layer and producing, in response to low energy gammas from the source, first gamma characterizing signals; and a high energy gamma detecting layer located downstream of the low energy gamma detecting layer and producing, in response to high energy gammas from the source, second gamma characterizing signals.

13. A multi-layer detector assembly as recited in claim 12, wherein at least one of said X-ray detecting layer, said low energy gamma detecting layer and said high energy gamma detecting layer is a scintillator and the characterizing signals produced by the scintillator include scintillation light, and wherein said multi-layer detector assembly further comprises a photodetector layer which producer in response to the visible light, a corresponding electric signal.

14. A multi-modality scanner comprising:

a gantry having a longitudinal axis;

a scanner operation controller;

at least one pair of diametrically opposite detector assemblies as recited in claim 1, the detector assemblies of said pair mutually facing each other and being connected to the scanner controller whereby the first, second and third radiation characterizing signals from said detector assemblies are supplied to said scanner operation controller;

a low energy gamma radiation source movably mounted to the gantry, and connected to and controlled by the scanner operation controller; and a collimator mounted rotatable to said gantry about the longitudinal axis, said collimator being connected to and controlled by said scanner operation controller.

15. A detector assembly as recited in claim 1, wherein said high energy gamma detector includes a second high-density scintillator.

16. A detector assembly as recited in claim 15, wherein said second high-density scintillator is a GSO scintillator.

17. A detector assembly for multi-modality scanners for detecting low energy radiation and first and second levels of high energy radiation emitted from a source under investigation, the detector assembly comprising:

a low energy radiation detector substantially transparent to the first and second levels of high energy radiation but responsive to the low energy radiation from the source, said low energy radiation detector producing, in response to said low energy radiation, first radiation characterizing signals;

a first high energy radiation detector located downstream from said low energy radiation detector and responsive to the first level of high energy radiation from the source, said first high energy radiation detector producing, in response to said first level of high energy radiation, second radiation characterizing signals; and a second high energy radiation, detector located downstream from said low energy radiation detector and responsive to the second level of high energy radiation from the source, said second high energy radiation detector producing, in response to the second level of high energy radiation, third radiation characterizing signals.

18. A detector assembly as recited in claim 17, wherein at least one of said low energy radiation detector, said first high energy radiation detector and said second high energy radiation detector comprises a scintillator.

19. A detector assembly as recited in claim 18, further comprising a photodetector optically coupled to said scintillator, said photodetector producing, in response to the radiation characterizing signals from said scintillator, corresponding electric signals.

20. A detector assembly as recited in claim 19, wherein the photodetector is selected form the group consisting of an avalanche photodiode, a pin diode and a photomultiplier tube.

21. A detector assembly as recited in claim 18, wherein the low energy radiation detector comprises a high-luminosity scintillator.

22. A detector assembly as recited in claim 21, wherein said high-luminosity scintillator is a CsI(TI) scintillator.

23. A detector assembly as recited in claim 17, wherein said first high energy radiation detector includes a first high-density scintillator.

24. A detector assembly as recited in claim 17, wherein said second high energy radiation detector includes a second high-density scintillator.

25. A detector assembly as recited in claim 23, wherein said first high-density scintillator comprises a LSO scintillator.

26. A detector assembly as recited in claim 24, wherein said second high-density scintillator is a GSO scintillator.

* * * * *